United States Patent [19]

McGrath et al.

[11] Patent Number: 5,493,002
[45] Date of Patent: Feb. 20, 1996

[54] ARYL ETHYNYL PHTHALIC ANHYDRIDES AND POLYMERS WITH TERMINAL OR PENDANT AMINES PREPARED WITH ARYL ETHYNYL PHTHALIC ANHYDRIDES

[75] Inventors: James E. McGrath; Gerald W. Meyer, both of Blacksburg, Va.

[73] Assignees: Virginia Tech Intellectual Properties, Inc.; Virginia Polytechnic Institute and State University, both of Blacksburg, Va.

[21] Appl. No.: 268,555

[22] Filed: Jul. 6, 1994

[51] Int. Cl.$^6$ ............................ C08G 69/08; C08L 77/04
[52] U.S. Cl. ........................ 528/310; 525/421; 525/436; 525/425
[58] Field of Search ........................ 528/310; 525/421, 525/436, 425

[56] References Cited

U.S. PATENT DOCUMENTS 4,128,588  12/1978  Sabourin et al. ...................... 568/939
4,131,625  12/1978  Arnold et al. ...................... 568/33

OTHER PUBLICATIONS

J. G. Smith, et al., Polymer Preprints, 35(1) 1994, 353–54.
G. W. Meyer, et al., Polymer Preprints, 35(1) 1994, 549–50.
Paul, et al., Abstracts of the IVth International Conference on Polyimides, Ellenville, N.Y., 1991, pp. 23–26.
Jayaraman, et al., Polymer Preprints 34, Mar. 1, 1993, pp. 511–512.
Jensen, et al., Polymer, 34:630–635 (1993).
Sabourin, et al., J. Org. Chem., 48:5135–5137 (1983).

*Primary Examiner*—Joseph L. Schofer
*Assistant Examiner*—I. Zemel
*Attorney, Agent, or Firm*—Whitham, Curtis, Whitham & McGinn

[57] ABSTRACT

Arylethynyl phthalic anhydrides have been synthesized and shown to have particular application as endcappers or pendant groups in high performance/high temperature thermosets which include amine terminal or amine pendant groups.

5 Claims, No Drawings

ARYL ETHYNYL PHTHALIC ANHYDRIDES AND POLYMERS WITH TERMINAL OR PENDANT AMINES PREPARED WITH ARYL ETHYNYL PHTHALIC ANHYDRIDES

BACKGROUND OF THE INVENTION

1. Field of the Invention

The invention is generally related to a new class of compounds identified as arylethynyl phthalic anhydrides. In addition, the invention is directed to polymers having pendant or terminal amines that are reacted with arylethynyl phthalic anhydrides to produce a high performance/high temperature resin having superior solvent resistance, heat resistance, and toughness properties.

2. Description of the Prior Art

There is a growing demand for thermosetting polymers that are processable, yet solvent resistant, and can withstand temperatures temperatures in excess of 700° F. (371 ° C.) for extended periods of time. Including an endcapping or pendant group at the end of a polymer chain or along the backbone of the polymer, respectively, which is capable of crosslinking or chain extension at high temperatures can provide a thermoset which has highly desirable solvent resistance and toughness properties. A chief requirement for the endcapping group or pendant group is that it not cure (e.g., undergo the crosslinking reaction) until after the onset of flow of the polymer. That is, the endcapping or pendant group must have a higher cure temperature than the melt temperature, $T_m$, and/or glass transition temperature, $T_g$, of the polymer. Presently available nadimide, maleimide, cyanate, and acetylene end cappers do not fit this criteria for many high performance/high temperature polymeric materials. Specifically, many high performance/high temperature polymeric materials have $T_g$'s that are higher than the cure temperature for these end cappers.

Recently, many laboratories have found that substituted ethynyl compounds are useful as plasticizers, endcappers or pendant groups. These compounds undergo addition reactions at high temperatures, thus they may allow the formation of heat and solvent resistant high performance/high temperature thermosets. For example, U.S. Pat. No. 4,131,625 to Arnold et al. discloses the use of 4,4-bis(3-ethynylphenoxy) diphenylsulfone as a plasticizer prepared from 3-ethynylphenol. U.S. Pat. No. 4,128,588 to Sabourin discloses the preparation of a nitrophenyl hydroxy substituted acetylene for use as an endcapper. Paul et al., *Abstracts of the IVth International Conference on Polyimides*, Ellenville, N.Y., 1991 discloses the use of 3-phenylethynyl aniline (PEA) as a high temperature curing endcapper. Jayaraman et al., *Polymer Preprints* 34, Mar. 1, 1993, p. 511 discloses the synthesis of 3-phenylethynyl phenol for use as an end capper to high temperature arylene ethers. Jensen et al., *Polymer*, 34:630–635 (1993) discloses the synthesis of polyimides with pendent ethynyl groups. Sabourin et al., *J. Org. Chem.*, 48:5135–5137 (1983) discloses the synthesis of 4-ethynylphthalic anhydride via 2-methyl-3-butyn-2-ol, but does not describe its utility.

SUMMARY OF THE INVENTION

It is an object of this invention to provide a new class of compounds which will be useful in the production of high performance/high temperature polymers.

According to the invention, compounds having the general formula:

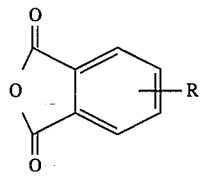

where R is covalently bonded at positions 3–6 of the phthalic anhydride and has the formula:

where X is a substituted or unsubstituted aryl group have been synthesized. These compounds cure at temperatures ranging between 380° C. and 420° C. Thus, these compounds will be very useful as endcappers or pendant groups in high performance/high temperature materials, since they will generally not cure until after flow of the polymer material. The compounds also have the advantages of having low melt viscosity and the ability to cure without the evolution of volatile byproducts.

DETAILED DESCRIPTION OF THE PREFERRED EMBODIMENTS OF THE INVENTION

Compounds having the general formula:

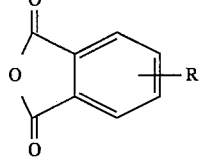

where R is covalently bonded at positions 3–6 of the phthalic anhydride and has the formula:

where X is a substituted or unsubstituted aryl group have been synthesized. In particular, substituted aryl groups would include phenyls and naphthyls with halogen (chlorine, fluorine, bromine, and iodine), nitro, amino, lower alkyl ($C_{1-4}$), esters, and other derivatives. The compounds can be used to endcap any amine-terminated polymer, including polyimides, polyamides, poly(arylene ethers), etc., and are particularly useful as endcappers for high $T_g$ amine terminated polymers. In addition, the compounds can be incorporated as pendant groups in the backbone of the polymer chain which has monomers with amino substituted pendant groups. The compounds have the advantage of undergoing a cure reaction at elevated temperatures between 380° C. and 420° C. Thus, high performance/high temperature polymers with the compounds of the present invention incorporated into the polymer as an endcapper or a pendant group along the backbone can advantageously be prepared since the compounds will not generally cure, depending on the polymer used, until after the onset of flow above $T_m$, and $T_g$ of the polymer.

Polymers which employ the compounds of this invention as endcappers are represented generally by the structure:

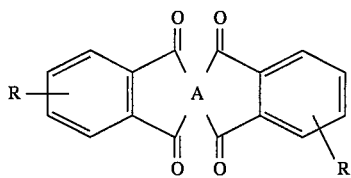

where A is an amine terminated polymer, and where R is covalently bonded at positions 3–6 of the phthalic anhydride and has the formula:

where X is a substituted or unsubstituted aryl group, and particularly includes phenyls and naphthyls substituted with halogens, nitro, amino, lower alkyl, ester and other moieties.

Polymers which employ the compounds of this invention as pendant groups along the polymer backbone have monomeric units represented generally by the structure:

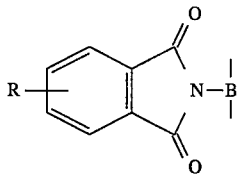

where B is a monomer including an amino substituted moiety, such as illustrated in the above structure, from reaction with the aryl ethynyl phthalic anhydride compounds of this invention, and where R is covalently bonded at positions 3–6 of the phthalic anhydride and has the formula:

where X is a substituted or unsubstituted aryl group, and particularly includes phenyls and naphthyls substituted with halogens, nitro, amino, lower alkyl, ester and other moieties.

Polyimides using the compounds of this invention as endcappers and as pendant groups along the polymer backbone have been synthesized. For example, copolymers which include dianhydrides, such as hexafluoroisopropylidene-2,2-bis (phthalic acid dianhydride)(6FDA) and bis[4-3,4-dicarboxyphenoxy)phenyl]propane dianhydride (BPA-DA), and diamines such as 1,4-phenylenediamine (p-PDA), 1,3-phenylenediamine (m-PDA), and 4,4'-oxydianyline (ODA) have been prepared with the compounds of the present invention covalently bonded to the amine-terminated ends of the copolymers. In addition, phenylethynyl phthalic arahydride succesfully reacted with pendant amines on copolymers of poly(arylene ether phosphine oxides) to produce phenylethynyl phenyl imides. In view of these results, a skilled artisan will recognize that a wide variety of polymers, and especially high performance/high temperature polymers, can be produced which include the compounds of the present invention covalently bonded to terminal or pendant amine groups of the polymer.

The compounds have particular application for use in conjunction with polymers having the following chemical structure:

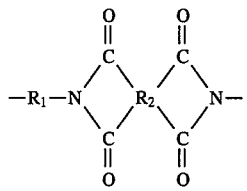

where exemplary structures for R1 and R2 are presented in Tables 1 and 2 respectively.

TABLE 1

DIAMINES IN THE COPOLYMER R1

(A) —⟨phenyl⟩— (PPDA)

(B) —⟨phenyl⟩— (mPDA) (meta)

(C) —⟨tolyl⟩—⟨tolyl⟩— (oTOLID) with $H_3C$ and $CH_3$ substituents (D) —⟨phenyl⟩—⟨phenyl⟩—⟨phenyl⟩— (DATP)

(E) —⟨phenyl⟩—O—⟨phenyl⟩— (DDE)

(F) —⟨phenyl⟩—S—⟨phenyl⟩— (DDS)

TABLE 1-continued

DIAMINES IN THE COPOLYMER R1

(G) —⟨phenyl⟩—CH₂—⟨phenyl⟩— (DDM)

(H) —⟨phenyl⟩—CH₃  (mDATOL)

(I) —⟨phenyl⟩—O—⟨phenyl⟩—⟨phenyl⟩—O—⟨phenyl⟩— (BAPB)

(J) —⟨phenyl⟩—O—⟨phenyl⟩—C(CH₃)₂—⟨phenyl⟩—O—⟨phenyl⟩— (DAFP)

(K) —⟨phenyl⟩—O—⟨phenyl⟩—C(CF₃)₂—⟨phenyl⟩—O—⟨phenyl⟩— (DAPFP)

(L) —⟨phenyl⟩—C(CH₃)₂—⟨phenyl⟩—C(CH₃)₂—⟨phenyl⟩— (Bis aniline P)

(M) —⟨phenyl⟩—C(CF₃)(phenyl)—⟨phenyl⟩— (3FDAM)

TABLE 2

DIANHYDRIDES IN THE COPOLYMER R₂

(1) ⟨phenyl⟩ PMDA (2) ⟨phenyl⟩—⟨phenyl⟩ BPDA (3) ⟨phenyl⟩—C(=O)—⟨phenyl⟩ BTDA (4) ⟨phenyl⟩—C(CF₃)₂—⟨phenyl⟩ 6FDA

TABLE 2-continued

DIANHYDRIDES IN THE COPOLYMER

Functionalizing polymers with the arylethynyl phthalic anhydrides of this invention imparts excellent thermooxidative stability and solvent resistance upon cure. Cured materials that utilize the arylethynyl phthalic anhydrides have been found to exhibit excellent high temperature adhesion to substrates. As discussed below in the Examples section, the synthesis of the compounds can readily be synthesized in a one-step method and are easily purified.

EXAMPLE 1

Synthesis of 4-Phenylethynylphthalic Anhydride 4-phenylethynylphthalic anhydride (4PEPA), was synthesized via the palladium catalyzed coupling reaction of 4-bromophthalic anhydride and phenylacetylene in the presence of triethylamine as solvent and dimethylacetamide (DMAc) as the cosolvents as shown in scheme 1.

scheme 1

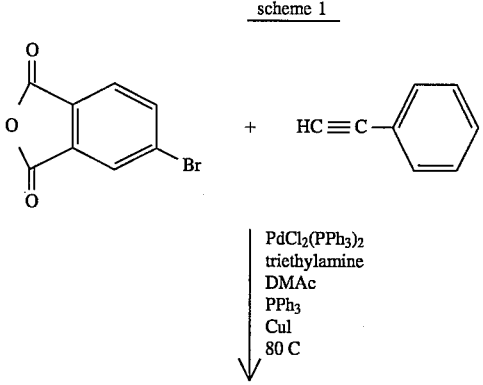

-continued
scheme 1

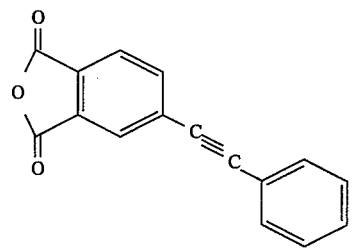

More specifically, $2.202 \times 10^{-2}$ moles (5.000 grams) of 4-bromophthalic anhydride (4-BrPAN) was charged to a round bottom flask equipped with a condenser, $N_2$ purge, and a magnetic stir bar, followed by the addition of 0.0465 grams of triphenylphosphine (PPh$_3$). Phenylacetylene ($2.202 \times 10^{-2}$ moles, 2.250 grams) was then syringed into the flask with 10 mL of DMAc, Pd(Cl$_2$)(PPh$_3$)$_2$ (0.0233 grams) was washed in the 10 mL of triethylamine. The flask was slowly heated to 60° C. and then 0.00925 grams of CuI was added with 15 mL of triethylamine. The reaction temperature was raised to and maintained at 80° C. for about 12 hours.

The reaction mixture was filtered to remove the inorganic salts formed. The triethylamine was removed under vacuum by a rotary evaporator. The solution was then poured into water. The aqueous solution was then acidified with dilute HCl to a pH of 4. A light yellow solid precipitated out of solution. The solid was extracted with ether. The ethereal solution was treated with charcoal, dried over MgSO$_4$, and filtered through Celite, a filter aid. The ether was removed under vacuum by rotary evaporator and crude 4-PEPA was obtained. The crude product was dried under vacuum at 85° C. for 24 hours. The crude 4-PEPA was then sublimed under vacuum at 160° C. which afforded an off-white yellow solid. Crude 4-PEPA may be recrystallized directly from refluxing acetic anhydride upon cooling. Overall yield (4.45 g, 84%), mp 146–148°, IR–cm$^{-1}$ 1776, 1847 (anhydride, C—O), 3050 (aromatic C—H), 2214 (—C≡C—), 1506 (aromatic C—C), $^1$H NMR (DMSO –d$_6$) 7.4–7.5 (m, 3H, aromatic), 7.6 (m, 2H, aromatic), 8.1 (s, 2H, aromatic) 8.2 (s, 1H, aromatic); MS m/z (relative intensity %); 248 (M+, 100).

EXAMPLE 2

Synthesis of Polymers With Terminal Amine Groups Being Reacted With 4 Phenylethynyl Phthalic Anhydride 4-phenylethynylphthalic anhydride terminated polyimide matrix resins have been synthesized using the ester acid route in high yields and purity. The materials were based on 6FDA, BPA-DA, p-PDA, and ODA, and three different molecular weights were generated ranging from 3,000 to 15,000 g/mole. Molecular weight control was achieved utilizing 4-phenylethynylphthalic anhydride as an endcapping agent. This afforded intrinsic viscosity values that corresponded very well with the increase in molecular weights of the 6FDA/p-PDA and 6FDA/ODA polyimide systems. Scheme 2 illustrates the general synthetic scheme for 4-phenylethynyl phthalic anhydride terminated polyimides.

reflux condenser heated in an oil bath, 7–10 ml absolute ethanol per gram dianhydride was then introduced. The mixture was then refluxed with stirring until a clear solution was obtained, at which time the trap was drained. When the distillation of ethanol ceased, the trap was filled with o-dichlorobenzene (o-DCB). 1.060×10$^{-3}$ moles (0.263 grams) 4-phenylethynylphthalic anhydride was then charged to control molecular weight with 9 ml of NMP, 1.021×10$^{-2}$ (1.103 grams) p-PDA was then charged into the reaction vessel, followed by 9 ml NMP and 5 ml o-DCB (80:20 volume to volume) to give a solids content of 20% weight per volume. The reaction mixture was then heated to 170–185° C. for 20 hours, after which time the polymer solution was coagulated by slowly dripping the polyimide solution into methanol in a high speed blender. The polymer was collected by suction filtration, washed with excess methanol and then excess anhydrous diethyl ether. The polymer was then air dried 6–8 hours and vacuum dried at about 160° C. for 24 hours.

The polymer materials appeared to be completely imidized, showing strong infrared imide absorptions at 1780 cm$^{-1}$, 1730 cm$^{-1}$, 1370 cm$^{-1}$, and 710 cm$^{-1}$, and the absence of absorptions attributable to amic acid. All of the polyimides formed tough, flexible films upon curing. Glass transition temperatures before curing were 258–340° C. and after

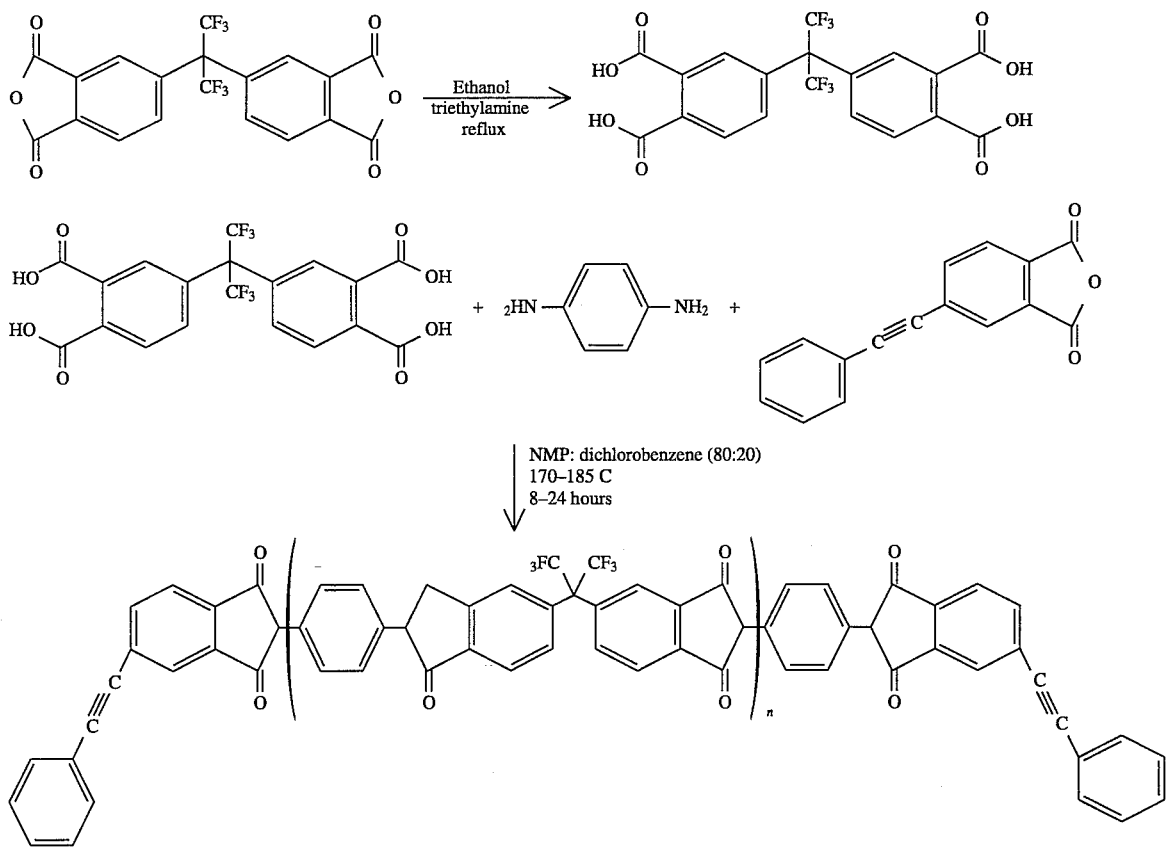

Polymerizations were conducted as follows for the synthesis of 6FDA/p-PDA with a number average molecular weight (Mn) of 10,000 g/mole as an example: 9.679×10$^{-3}$ moles (4,300 grams) monomer grade 6FDA was charged to a 3-neck round bottom flask equipped with a magnetic stirrer, nitrogen inlet, thermometer, reverse Dean-Stark trap and curing were 310–362° C., which is consistent with the T$_g$ of the high molecular weight linear systems. The 3,000 g/mole 6FDA/p-PDA system appears to be crystalline, based on differential scanning calorimetry (DSC) melting transition and wide angle X-ray studies. The onset of crosslinking occurs at approximately 380–420° C.

The thermal stability of the acetylene terminated polyimides was investigated by subjecting the cured samples to dynamic thermal gravimetric analysis (TGA). 5% weight loss data with values of 537–555° C. by TGA were determined. Thermally cured samples also display good solvent resistance when immersed in DMAc.

EXAMPLE 3

Synthesis of Polymers With Pendant Amine Groups Being Reacted With 4 Phenylethynyl Phthalic Anhydride Pak et al., *Polymer (London)* 34(4), 885, 1993, which is herein incorporated by reference, fully describes the synthesis of amino bis(4-fluorophenyl)phenylphosphine oxide (amino DFTPPO) and the synthesis of poly(arylene ether) phosphine oxide copolymer with pendant amines. The reaction sequence is summarized below in scheme 3.

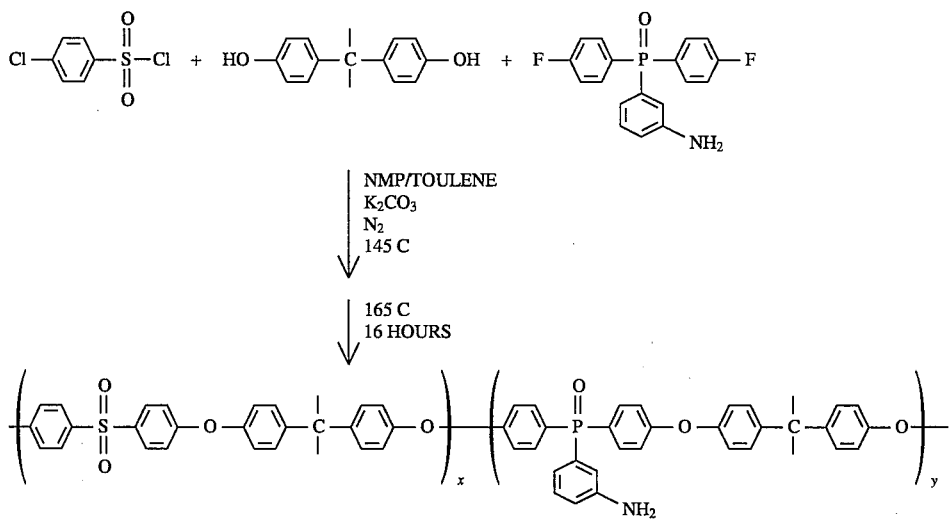

It has been discovered that the phyenylthynyl phthalic anhydride described in Example 1 will also react with pendant aryl amines on copolymers of poly(arylene ether phosphine oxides) to produce pendant phenylethynyl phenylimides according to scheme 4.

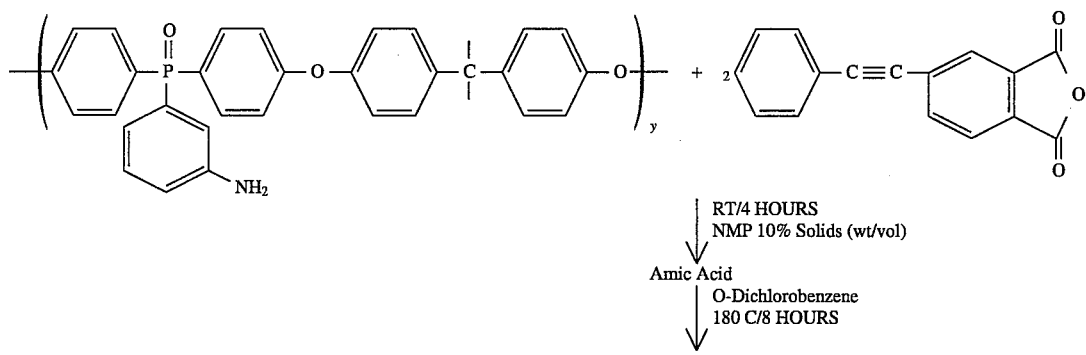

-continued
scheme 4

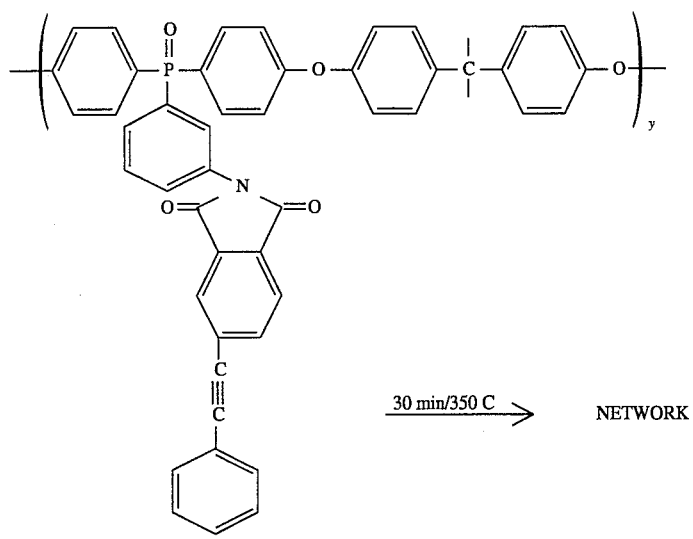

$\xrightarrow{\text{30 min/350 C}}$ NETWORK

In summary, to a four neck round bottom flask equipped with a mechanical stirrer, nitrogen inlet, thermometer, and a reverse dean stark trap with a condenser was added 5.5 g ($1.2\times10^{-3}$ mols) of 5%, 10%, or 20% pendant amino poly(arylene ether phosphine oxide) copolymer along with 55 ml (20 wt % solids) of NMP. The contents was allowed to stir at room temperature until a homogenous solution was obtained. Then, 0.577 g ($2.0\times10^{-3}$ mols) of phenylethynylphthalic anhydride was charged into the flask and allowed to stir at room temperature for an additional 4 hours, after which 11 ml of o-dichlorobenzene was added and the solution was heated at 180° C. for 8 hours. The resulting polymer with pendant phenylethynyl phenylimides was cooled and then coagulated into excess methanol two times and dried in a vacuum oven at 100° C. for 8 hours.

Table 5 presents the characterization of poly(arylene ether) containing pendant phenyethynylimides produced according to this technique.

TABLE 5

| Polymer | [η] 25° C. CHCl₃ dl/g | <Mn> Amine (g/mole) | Tg (°C.) Uncured | Tg (°C.) Cured | % Gel Fraction |
|---|---|---|---|---|---|
| PEPO Control | 1.09 | — | — | — | 0 |
| 5% Amino PEPO | 1.01 | 9,700 | 201 | 201 | 93 |
| 10% Amino PEPO | .99 | 4,700 | 201 | 207 | 98 |
| 20% Amino PEPO | .81 | 2,500 | 201 | 218 | 99 |

The intrinsic viscosity values indicate that high molecular weight polymers were synthesized. The $T_g$ of the pendant amine polymers increased slightly as the concentration of the amines on the backbone increased. Gelation studies shows that the phenylethynyl polymer reacts nicely to afford networks with increased solvent resistance.

The Examples demonstrate that polyimide oligomers endcapped by reacting 4-phenylethynyl phthalic anhydride with amino terminal groups and polymers with amino-pendant groups reacted with 4-phenylethynyl phthalic anhydride can be synthesized via a "one pot" solution imidization involving ester-acid and diamine monomers to yield a highly imidized, controlled molecular weight phenylethynyl phthalic functionalized polyimides. Upon curing, insoluble, highly crosslinked films with high $T_g$ values can be obtained which exhibit excellent thermooxidative stability. The wide processing window afforded by the phenylethynyl phtalic compounds makes them ideal for use with high temperature thermosets.

While the invention has been described in terms of its preferred embodiments, those skilled in the art will recognize that the invention can be practiced with modification within the spirit and scope of the appended claims.

We claim:

1. A polymer compound having the formula:

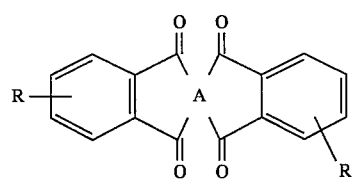

where A is an amine terminated polymer, and where R is covalently bonded at positions 3–6 of the phthalic anhydride and has the formula:

where X is a substituted or unsubstituted aryl group.

2. The polymer compound of claim 1 wherein X is a substituted or unsubstituted phenyl.

3. The polymer compound of claim 1 wherein R is covalently bonded at positions 4 or 5 of the phthalic anhydride.

4. The polymer compound of claim 4 wherein a is selected from the group consisting of polyimides, polyamides, and poly(arylene ethers).

5. A polymer compound comprising a polymeric chain including a monomeric unit, said monomeric unit having the formula:

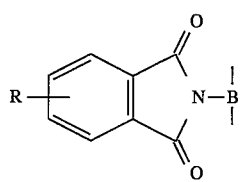
where B is a monomer including an amino substituted group, and where R is covalently bonded at positions 3–6 of the phthalic anhydride and has the formula:
—c≡c—x
where X is a substituted or substituted aryl group.
* * * * *